US006245776B1

(12) United States Patent
Skwierczynski et al.

(10) Patent No.: US 6,245,776 B1
(45) Date of Patent: *Jun. 12, 2001

(54) FORMULATIONS AND METHODS FOR TREATMENT OF MUCOSAL ASSOCIATED CONDITIONS WITH AN IMMUNE RESPONSE MODIFIER

(75) Inventors: Raymond D. Skwierczynski, Oakdale, MN (US); Kenneth R. Phares, Chapel Hill, NC (US); Richard L. Miller, Maplewood, MN (US); Zheng Jane Li, Quaker Hill, CT (US); Michael J. Jozwiakowski, Stillwater; Terri F. Busch, St. Paul, both of MN (US)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/479,578

(22) Filed: Jan. 7, 2000

Related U.S. Application Data

(60) Provisional application No. 60/115,256, filed on Jan. 8, 1999.

(51) Int. Cl.⁷ .................................................. A61K 31/44
(52) U.S. Cl. .......................................................... 514/293
(58) Field of Search ............................................ 514/293

(56) References Cited

U.S. PATENT DOCUMENTS

| | | |
|---|---|---|
| 3,314,941 | 4/1967 | Littell et al. . |
| 3,917,624 | 11/1975 | El-Haj et al. . |
| 4,689,338 * | 8/1987 | Gerster ................................ 514/293 |
| 4,698,348 | 10/1987 | Gerster . |
| 4,929,624 | 5/1990 | Gerster et al. . |
| 4,988,815 | 1/1991 | Andre et al. . |
| 5,037,986 | 8/1991 | Gerster . |
| 5,175,296 | 12/1992 | Gerster . |
| 5,238,944 * | 8/1993 | Wick et al. ........................... 514/293 |
| 5,266,575 | 11/1993 | Gerster et al. . |
| 5,268,376 | 12/1993 | Gerster . |
| 5,346,905 | 9/1994 | Gerster . |
| 5,352,784 | 10/1994 | Nikolaides et al. . |
| 5,367,076 | 11/1994 | Gerster . |
| 5,389,640 * | 2/1995 | Gerster et al. ....................... 514/293 |
| 5,395,937 | 3/1995 | Nikolaides et al. . |
| 5,444,065 | 8/1995 | Nikolaides et al. . |
| 5,446,153 | 8/1995 | Lindstrom et al. . |
| 5,482,936 | 1/1996 | Lindstrom . |
| 5,494,916 | 2/1996 | Lindstrom et al. . |
| 5,525,612 | 6/1996 | Gerster . |
| 5,585,612 | 12/1996 | Harp, Jr. . |
| 5,605,899 | 2/1997 | Gerster et al. . |
| 5,627,281 | 5/1997 | Nikolaides et al. . |
| 5,644,063 | 7/1997 | Lindstrom et al. . |
| 5,648,516 | 7/1997 | Nikolaides et al. . |
| 5,714,608 | 2/1998 | Gerster . |
| 5,741,908 | 4/1998 | Gerster et al. . |
| 5,741,909 | 4/1998 | Gerster et al. . |
| 5,886,006 | 3/1999 | Nikolaides et al. . |
| 5,977,366 | 11/1999 | Gerster et al. . |
| 6,069,149 | 5/2000 | Nanba et al. . |

FOREIGN PATENT DOCUMENTS

| | | |
|---|---|---|
| 0 894 797 A1 | 2/1998 | (EP) . |
| 9-208584 | 8/1997 | (JP) . |
| 93-09119 | 5/1993 | (WO) . |
| 97-41884 | 11/1997 | (WO) . |
| 97-48704 | 12/1997 | (WO) . |
| 98-24436 | 6/1998 | (WO) . |
| 99/29693 | 6/1999 | (WO) . |
| 00-06577 | 2/2000 | (WO) . |
| 00-09506 | 2/2000 | (WO) . |

OTHER PUBLICATIONS

R. Snoeck, G. Andrei and E. De Clercq, "Specific Therapies for Human Papilloma Virus Infections", *Current Opionion in Infectious Diseases*, 1998, vol. 11, pp. 733–737.

"3M Pharmaceuticals unveils research and development and expansion plans" retrieved from STN INTERNATIONAL, No. 2138, p. 10–... (1996).

Harrison, C.J. et al., "Effects of Cytokines and R–837 a Cytokine Inducer on UV–Irradiation Augmented Recurrent Genital Herpes in Guinea–Pigs", *Antiviral Research*, 1991, vol. 15, No. 4, pp. 315–322.

Harrison, C.J. et al., "Modification of Immunological Responses and Clinical Disease During Topical R–837 treatment of Genital HSV–2 Infection", *Antiviral Research*, 1988, vol. 10, No. 4–5, pp. 209–224.

Miller, R.L. et al., Review Article. Imiquimod Applied Topically: A Novel Immune Response Modifier and New Class of Drug, *International Journal of Immunopharmacology*, Jan. 1999 (1999–01), vol. 21, No. 4–5, pp. 1–14.

Chollet, J.L. et al., "Development of a Topically Active Imiquimod Formulation", *Pharmaceutical Development and Technology*, New York, NY, US Jan. 1999 (1999–01), vol. 4, No. 1, pp. 35–43.

(List continued on next page.)

*Primary Examiner*—Raymond Henley, III
(74) *Attorney, Agent, or Firm*—MarySusan Howard; Ted K. Ringsred; Robert W. Sprague

(57) ABSTRACT

Immune response modifier (IRM) compounds—imidazoquinoline amines, imidazopyridine amines, 6,7-fused cycloalkylimidazopyridine amines, 1,2-bridged imidazoquinoline amines, thiazolo- and oxazolo-quinolinamines and pyridinamines, imidazonaphthyridine and tetrahydroimidazonaphthyridine amines—are useful for the treatment of conditions at and below the mucosal surfaces by administering a therapeutically effective amount of such compounds to the mucosal surface. Novel pharmaceutical formulations are provided. In one embodiment, the pharmaceutical formulations are advantageous for treatment of cervical conditions such as cervical dysplasias including cervical intraepithelial neoplasias.

22 Claims, 3 Drawing Sheets

OTHER PUBLICATIONS

Dittgen, M. et al., "Acrylic Polymers. A review of Pharmaceutical Applications", *STP Pharma Pratiques*, Paris, FR, (1997) vol. 7, No. 6, pp. 403–437.

Wozniak, et al., "The Amination of 3–nitro–1, 5–naphthyridines by Liquid Ammonia/Potassium Permanganate[1,2]. A New and Convenient Amination Method." Journal of the Royal Netherlands Chemical Society, 102, pp. 511–513, Dec. 12, 1983.

Brennan, et al., "Automated Bioassay of Interferons in Micro–test Plates", *Biotechniques*, Jun./Jul., 78, 1983.

Testerman, et al., "Cytokine Induction by the Immunomodulators Imiquimod and S–27609", Journal of *Leukocyte Biology*, vol. 58, pp. 365–372, Sep. 1995.

Bachman, et al., "Synthesis of Substituted Quninolylamines. Derivatives of 4–Amino–7–Chloroquinoline", J. Org. Chem., 15, pp. 1278–1284 (1950).

Jain, etal., "Chemical and Pharmacological Investigations of Some ω–Substituted Alkylamino–3–aminopyridines", J. Med. Chem., 11, pp. 87–92 (1968).

Baranov, et al., Chem. Abs. 85, 94371, (1976).

Berényi, et al., "Ring Transformation of Condensed Dihydro–as–triazines", *J. Heterocyclic Chem.*, 18, pp. 1537–1540 (1981).

* cited by examiner

US 6,245,776 B1

FORMULATIONS AND METHODS FOR TREATMENT OF MUCOSAL ASSOCIATED CONDITIONS WITH AN IMMUNE RESPONSE MODIFIER

This application claims priority from U.S. Provisional Application Ser. No. 60/115,256, filed Jan. 8, 1999.

FIELD OF THE INVENTION

The present invention relates to pharmaceutical formulations and methods for application of immunomodifying imidazoquinoline amines, imidazopyridine amines, 6,7-fused cycloalkylimidazopyridine amines, 1,2-bridged imidazoquinoline amine, thiazolo- and oxazolo-quinolinamines and pyridinamines, imidazonaphthyridine and tetrahydroimidazonaphthyridine amines to a mucosal surface. In one embodiment, the invention provides formulations and methods which are particularly advantageous for topical application to the cervix for treatment of cervical conditions such as cervical dysplasias including dysplasia associated with human papillomavirus (HPV).

BACKGROUND

Many imidazoquinoline amine, imidazopyridine amine, 6,7-fused cycloalkylimidazopyridine amine, 1,2-bridged imidazoquinoline amine, thiazolo- and oxazolo-quinolinamines and pyridinamines, imidazonaphthyridine and tetrahydroimidazonaphthyridine amine compounds have demonstrated potent immunostimulating, antiviral and antitumor (including anticancer) activity, and have also been shown to be useful as vaccine adjuvants to enhance protective immune system response to vaccines. These compounds are hereinafter sometimes collectively referred to as the "IRM" (immune response modifier) compounds of the invention. Such compounds are disclosed in, for example, U.S. Pat. Nos. 4,689,338, 5,389,640, 5,268,376, 4,929,624, 5,266,575, 5,352,784, 5,494,916, 5,482,936, 5,346,905, 5,395,937, 5,238,944, 5,525,612, WO99/29693 and U.S. Ser. No. 09/361,544 wherein their immunostimulating, antiviral and antitumor activities are discussed in detail, and certain specific diseases are identified as being susceptible to treatment therewith, including basal cell carcinoma, eczema, essential thrombocythaemia, hepatitis B, multiple sclerosis, neoplastic diseases, psoriasis, rheumatoid arthritis, type I herpes simplex, type II herpes simplex, and warts. One of these IRM compounds, known as imiquimod, has been commercialized in a topical formulation, Aldara™, for the treatment of anogenital warts associated with human papillomavirus.

The mechanism for the antiviral and antitumor activity of these IRM compounds is thought to be due in substantial part to enhancement of the immune response due to induction of various important cytokines (e.g., interferons, interleukins, tumor necrosis factor, etc.). Such compounds have been shown to stimulate a rapid release of certain monocyte/macrophage-derived cytokines and are also capable of stimulating B cells to secrete antibodies which play an important role in these IRM compounds' antiviral and antitumor activities. One of the predominant immunostimulating responses to these compounds is the induction of interferon (IFN)-$\alpha$ production, which is believed to be very important in the acute antiviral and antitumor activities seen. Moreover, up regulation of other cytokines such as, for example, tumor necrosis factor (TNF), IL-1 and IL-6 also have potentially beneficial activities and are believed to contribute to the antiviral and antitumor properties of these compounds.

Although some of the beneficial effects of IRM's are known, the ability to provide therapeutic benefit via topical application of an IRM for treatment of a particular condition at a particular location may be hindered due to tissue irritation, formulation wash away, poor permeation or undesired systemic delivery of the topically applied compound. Accordingly, there is a need for new methods and formulations to provide the greatest therapeutic benefit from this class of compounds.

SUMMARY OF THE INVENTION

It will be appreciated that at several locations throughout the specification, guidance is provided through lists of examples. In each instance, the recited list serves only as a representative group; it is not meant that the list is exclusive.

The present disclosure provides pharmaceutical formulations containing immune response modifier ("IRM") compounds and methods for treatment of conditions associated with a mucosal surface. The methods and formulations of the invention may be particularly advantageous for treatment of cervical conditions such as cervical dysplasias including cervical intraepithelial neoplasia.

Particularly preferred IRM compounds suitable for the pharmaceutical formulations of the invention include 4-amino-2-ethoxymethyl-$\alpha,\alpha$-dimethyl-1H-imidazo[4,5-c]quinoline-1-ethanol and 1-(2-methylpropyl)-1H-imidazo[4,5-c]quinolin-4-amine (known as imiquimod).

The IRMs can be formulated for application to a mucosal membrane, particularly the cervical mucosa.

DETAILED DESCRIPTION

Figure 1:
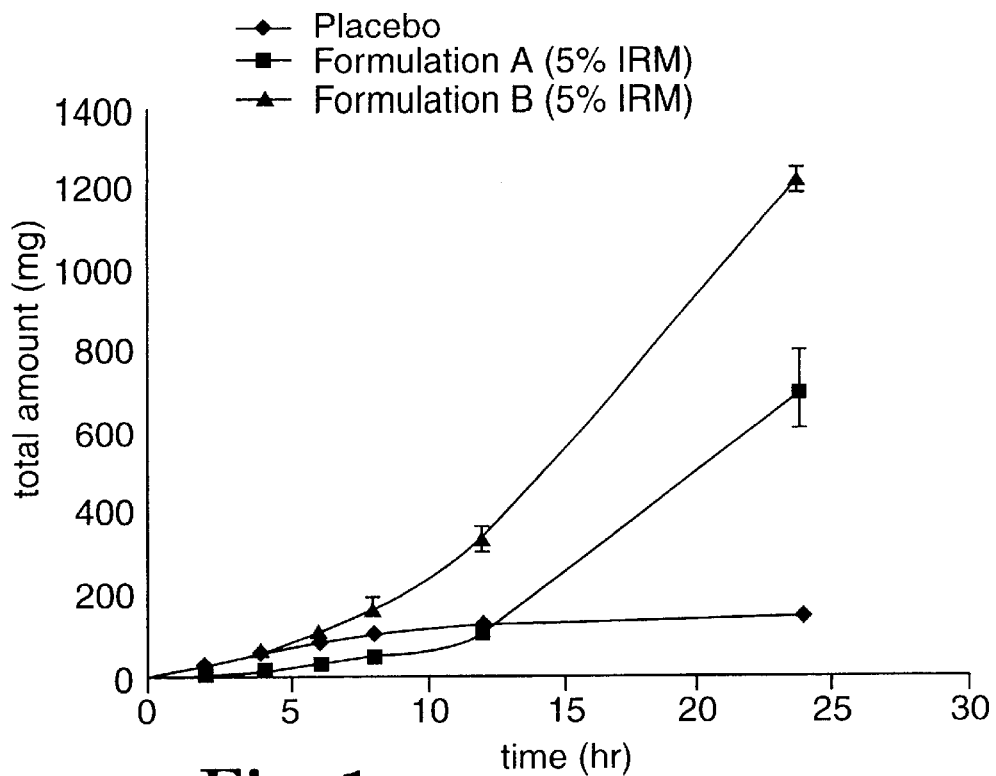
FIG. 1 is a graph comparing imiquimod transport across hairless mouse skin from three pharmaceutical formulations each containing 5% imiquimod.

The present invention is directed to methods and pharmaceutical formulations for effective treatment or prophylaxis of a mucosal associated condition. As used herein, a "mucosal associated condition" means an inflammatory, infectious, neoplastic or other condition that involves a mucosal surface or that is in sufficient proximity to a mucosal surface to be affected by a therapeutic or prophylactic agent topically applied to the mucosal surface.

In one embodiment, the invention provides new methods for using immune response modifier (IRM) compounds to treat or prevent conditions associated with a mucosal surface. For example, the invention provides IRM formulations which can advantageously be applied to the mucosal surface of the cervix to treat cervical conditions including cervical dysplasias such as cervical intraepithelial neoplasia.

In some preferred embodiments, the novel formulations are particularly advantageous for application of an IRM compound to a mucosal surface. In some such embodiments, the formulations can enhance therapeutic efficiency of the IRM by facilitating mucosal permeation or increasing the duration of contact of the IRM with the mucosal surface. The invention also provides pharmaceutical formulations containing a preservative system that renders the formulations suitable for packaging in multiple-use containers.

Preferred IRM Compounds

As noted above, many of the imidazoquinoline amine, imidazopyridine amine, 6,7-fused cycloalkylimidazopyridine amine, 1,2-bridged imidazoquinoline amine, thiazolo- and oxazolo-quinolinamines and pyridinamines, imidazonaphthyridine and tetrahydroimidazonaphthyridine amine IRM compounds of the present invention have demonstrated significant immunomodulating activity. Preferred immune response modifier compounds of the invention include 1H-imidazo[4,5-c]quinolin-4-amines defined by one of Formulas I–V below:

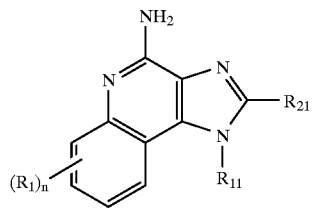

I wherein $R_{11}$ is selected from the group consisting of alkyl of one to ten carbon atoms, hydroxyalkyl of one to six carbon atoms, acyloxyalkyl wherein the acyloxy moiety is alkanoyloxy of two to four carbon atoms or benzoyloxy, and the alkyl moiety contains one to six carbon atoms, benzyl, (phenyl)ethyl and phenyl, said benzyl, (phenyl)ethyl or phenyl substituent being optionally substituted on the benzene ring by one or two moieties independently selected from the group consisting of alkyl of one to four carbon atoms, alkoxy of one to four carbon atoms and halogen, with the proviso that if said benzene ring is substituted by two of said moieties, then said moieties together contain no more than six carbon atoms;

$R_{21}$ is selected from the group consisting of hydrogen, alkyl of one to eight carbon atoms, benzyl, (phenyl)ethyl and phenyl, the benzyl, (phenyl)ethyl or phenyl substituent being optionally substituted on the benzene ring by one or two moieties independently selected from the group consisting of alkyl of one to four carbon atoms, alkoxy of one to four carbon atoms and halogen, with the proviso that when the benzene ring is substituted by two of said moieties, then the moieties together contain no more than six carbon atoms; and each $R_1$ is independently selected from the group consisting of alkoxy of one to four carbon atoms, halogen, and alkyl of one to four carbon atoms, and n is an integer from 0 to 2, with the proviso that if n is 2, then said $R_1$ groups together contain no more than six carbon atoms;

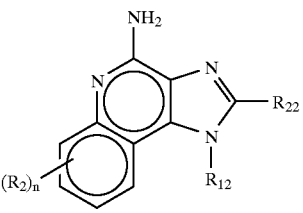

II wherein $R_{12}$ is selected from the group consisting of straight chain or branched chain alkenyl containing two to ten carbon atoms and substituted straight chain or branched chain alkenyl containing two to ten carbon atoms, wherein the substituent is selected from the group consisting of straight chain or branched chain alkyl containing one to four carbon atoms and cycloalkyl containing three to six carbon atoms; and cycloalkyl containing three to six carbon atoms substituted by straight chain or branched chain alkyl containing one to four carbon atoms; and $R_{22}$ is selected from the group consisting of hydrogen, straight chain or branched chain alkyl containing one to eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl containing one to four carbon atoms, straight chain or branched chain alkoxy containing one to four carbon atoms, and halogen, with the proviso that when the benzene ring is substituted by two such moieties, then the moieties together contain no more than six carbon atoms; and each $R_2$ is independently selected from the group consisting of straight chain or branched chain alkoxy containing one to four carbon atoms, halogen, and straight chain or branched chain alkyl containing one to four carbon atoms, and n is an integer from zero to 2, with the proviso that if n is 2, then said $R_2$ groups together contain no more than six carbon atoms;

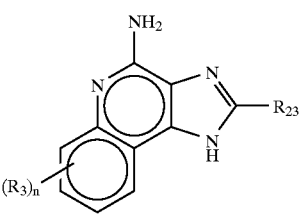

III wherein $R_{23}$ is selected from the group consisting of hydrogen, straight chain or branched chain alkyl of one to eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl of one to four carbon atoms, straight chain or branched chain alkoxy of one to four carbon atoms, and halogen, with the proviso that when the benzene ring is substituted by two such moieties, then the moieties together contain no more than six carbon atoms; and each R₃ is independently selected from the group consisting of straight chain or branched chain alkoxy of one to four carbon atoms, halogen, and straight chain or branched chain alkyl of one to four carbon atoms, and n is an integer from zero to 2, with the proviso that if n is 2, then said R₃ groups together contain no more than six carbon atoms;

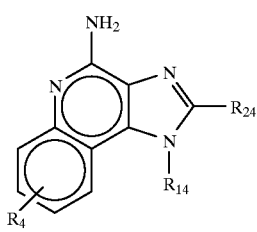

IV wherein

R₁₄ is —CHR$_x$R$_y$, wherein R$_y$ is hydrogen or a carbon-carbon bond, with the proviso that when R$_y$ is hydrogen R$_x$ is alkoxy of one to four carbon atoms, hydroxyalkoxy of one to four carbon atoms, 1-alkynyl of two to ten carbon atoms, tetrahydropyranyl, alkoxyalkyl wherein the alkoxy moiety contains one to four carbon atoms and the alkyl moiety contains one to four carbon atoms, 2-, 3-, or 4-pyridyl, and with the further proviso that when R$_y$ is a carbon—carbon bond R$_y$ and R$_x$ together form a tetrahydrofuranyl group optionally substituted with one or more substituents independently selected from the group consisting of hydroxy and hydroxyalkyl of one to four carbon atoms;

R₂₄ is selected from the group consisting of hydrogen, alkyl of one to four carbon atoms, phenyl, and substituted phenyl wherein the substituent is selected from the group consisting of alkyl of one to four carbon atoms, alkoxy of one to four carbon atoms, and halogen; and R₄ is selected from the group consisting of hydrogen, straight chain or branched chain alkoxy containing one to four carbon atoms, halogen, and straight chain or branched chain alkyl containing one to four carbon atoms;

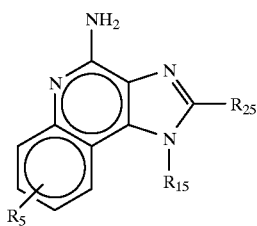

V wherein

R₁₅ is selected from the group consisting of: hydrogen; straight chain or branched chain alkyl containing one to ten carbon atoms and substituted straight chain or branched chain alkyl containing one to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; straight chain or branched chain alkenyl containing two to ten carbon atoms and substituted straight chain or branched chain alkenyl containing two to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to four carbon atoms, alkoxy of one to four carbon atoms, and halogen, with the proviso that when said benzene ring is substituted by two of said moieties, then the moieties together contain no more than six carbon atoms;

R₂₅ is

wherein

R$_S$ and R$_T$ are independently selected from the group consisting of hydrogen, alkyl of one to four carbon atoms, phenyl, and substituted phenyl wherein the substituent is selected from the group consisting of alkyl of one to four carbon atoms, alkoxy of one to four carbon atoms, and halogen;

X is selected from the group consisting of alkoxy containing one to four carbon atoms, alkoxyalkyl wherein the alkoxy moiety contains one to four carbon atoms and the alkyl moiety contains one to four carbon atoms, hydroxyalkyl of one to four carbon atoms, haloalkyl of one to four carbon atoms, alkylamido wherein the alkyl group contains one to four carbon atoms, amino, substituted amino wherein the substituent is alkyl or hydroxyalkyl of one to four carbon atoms, azido, chloro, hydroxy, 1-morpholino, 1-pyrrolidino, alkylthio of one to four carbon atoms; and R₅ is selected from the group consisting of hydrogen, straight chain or branched chain alkoxy containing one to four carbon atoms, halogen, and straight chain or branched chain alkyl containing one to four carbon atoms;

or a pharmaceutically acceptable salt of any of the foregoing.

Preferred 6,7 fused cycloalkylimidazopyridine amine IRM compounds are defined by Formula VI below:

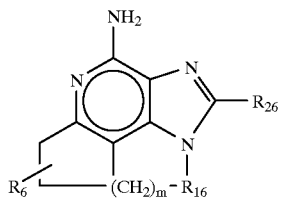

wherein m is 1, 2, or 3;

$R_{16}$ is selected from the group consisting of hydrogen; cyclic alkyl of three, four, or five carbon atoms; straight chain or branched chain alkyl containing one to ten carbon atoms and substituted straight chain or branched chain alkyl containing one to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; fluoro- or chloroalkyl containing from one to ten carbon atoms and one or more fluorine or chlorine atoms; straight chain or branched chain alkenyl containing two to ten carbon atoms and substituted straight chain or branched chain alkenyl containing two to ten carbon atoms, wherein the substituent is selected from the group consisting of cycloalkyl containing three to six carbon atoms and cycloalkyl containing three to six carbon atoms substituted by straight chain or branched chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms, with the proviso that any such alkyl, substituted alkyl, alkenyl, substituted alkenyl, hydroxyalkyl, alkoxyalkyl, or acyloxyalkyl group does not have a fully carbon substituted carbon atom bonded directly to the nitrogen atom; benzyl; (phenyl)ethyl; and phenyl; said benzyl, (phenyl)ethyl or phenyl substituent being optionally substituted on the benzene ring by one or two moieties independently selected from the group consisting of alkyl of one to four carbon atoms, alkoxy of one to four carbon atoms, and halogen, with the proviso that when said benzene ring is substituted by two of said moieties, then the moieties together contain no more than six carbon atoms;

and —$CHR_xR_y$ wherein $R_y$ is hydrogen or a carbon-carbon bond, with the proviso that when $R_y$ is hydrogen $R_x$ is alkoxy of one to four carbon atoms, hydroxyalkoxy of one to four carbon atoms, 1-alkynyl of two to ten carbon atoms, tetrahydropyranyl, alkoxyalkyl wherein the alkoxy moiety contains one to four carbon atoms and the alkyl moiety contains one to four carbon atoms, 2-, 3-, or 4-pyridyl, and with the further proviso that when $R_y$ is a carbon-carbon bond $R_y$ and $R_x$ together form a tetrahydrofuranyl group optionally substituted with one or more substituents independently selected from the group consisting of hydroxy and hydroxyalkyl of one to four carbon atoms, $R_{26}$ is selected from the group consisting of hydrogen, straight chain or branched chain alkyl containing one to eight carbon atoms, straight chain or branched chain hydroxyalkyl containing one to six carbon atoms, morpholinoalkyl, benzyl, (phenyl)ethyl and phenyl, the benzyl, (phenyl)ethyl or phenyl substituent being optionally substituted on the benzene ring by a moiety selected from the group consisting of methyl, methoxy, and halogen; and —$C(R_S)(R_T)(X)$ wherein $R_S$ and $R_T$ are independently selected from the group consisting of hydrogen, alkyl of one to four carbon atoms, phenyl, and substituted phenyl wherein the substituent is selected from the group consisting of alkyl of one to four carbon atoms, alkoxy of one to four carbon atoms, and halogen;

X is selected from the group consisting of alkoxy containing one to four carbon atoms, alkoxyalkyl wherein the alkoxy moiety contains one to four carbon atoms and the alkyl moiety contains one to four carbon atoms, haloalkyl of one to four carbon atoms, alkylamido wherein the alkyl group contains one to four carbon atoms, amino, substituted amino wherein the substituent is alkyl or hydroxyalkyl of one to four carbon atoms, azido, alkylthio of one to four carbon atoms, and morpholinoalkyl wherein the alkyl moiety contains one to four carbon atoms, and $R_6$ is selected from the group consisting of hydrogen, fluoro, chloro, straight chain or branched chain alkyl containing one to four carbon atoms, and straight chain or branched chain fluoro- or chloroalkyl containing one to four carbon atoms and at least one fluorine or chlorine atom;

and pharmaceutically acceptable salts thereof.

Preferred imidazopyridine amine IRM compounds are defined by Formula VII below:

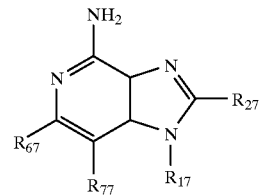

wherein $R_{17}$ is selected from the group consisting of hydrogen; —$CH_2R_W$ wherein $R_W$ is selected from the group consisting of straight chain, branched chain, or cyclic alkyl containing one to ten carbon atoms, straight chain or branched chain alkenyl containing two to ten carbon atoms, straight chain or branched chain hydroxyalkyl containing one to six carbon atoms, alkoxyalkyl wherein the alkoxy moiety contains one to four carbon atoms and the alkyl moiety contains one to six carbon atoms, and phenylethyl; and —$CH=CR_ZR_Z$ wherein each $R_Z$ is independently straight chain, branched chain, or cyclic alkyl of one to six carbon atoms;

$R_{27}$ is selected from the group consisting of hydrogen, straight chain or branched chain alkyl containing one to eight carbon atoms, straight chain or branched chain hydroxyalkyl containing one to six carbon atoms, alkoxyalkyl wherein the alkoxy moiety contains one to four carbon atoms and the alkyl moiety contains one to six carbon atoms, benzyl, (phenyl)ethyl and phenyl, the benzyl, (phenyl)ethyl or phenyl substituent being optionally substituted on the benzene ring by a moiety selected from the group consisting of methyl, methoxy, and halogen; and morpholinoalkyl wherein the alkyl moiety contains one to four carbon atoms;

$R_{67}$ and $R_{77}$ are independently selected from the group consisting of hydrogen and alkyl of one to five carbon atoms, with the proviso that $R_{67}$ and $R_{77}$ taken together contain no more than six carbon atoms, and with the further proviso that when $R_{77}$ is hydrogen then $R_{67}$ is other than hydrogen and $R_{27}$ is other than hydrogen or morpholinoalkyl, and with the further proviso that when $R_{67}$ is hydrogen then $R_{77}$ and $R_{27}$ are other than hydrogen;

and pharmaceutically acceptable salts thereof.

Preferred 1,2-bridged imidazoquinoline amine IRM compounds are defined by Formula VIII below:

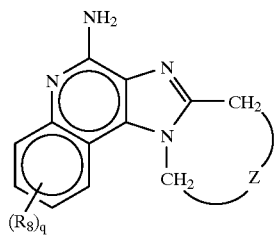

VIII wherein

Z is selected from the group consisting of:
—$(CH_2)_p$— wherein p is 1 to 4;
—$(CH_2)_a$—$C(R_DR_E)(CH_2)_b$—, wherein a and b are integers and a+b is 0 to 3, $R_D$ is hydrogen or alkyl of one to four carbon atoms, and $R_E$ is selected from the group consisting of alkyl of one to four carbon atoms, hydroxy, —$OR_F$ wherein $R_F$ is alkyl of one to four carbon atoms, and —$NR_GR'_G$ wherein $R_G$ and $R'_G$ are independently hydrogen or alkyl of one to four carbon atoms; and
—$(CH_2)_a$—$(Y)$—$(CH_2)_b$— wherein a and b are integers and a+b is 0 to 3, and Y is O, S, or —$NR_J$— wherein $R_J$ is hydrogen or alkyl of one to four carbon atoms;

and wherein q is 0 or 1 and $R_8$ is selected from the group consisting of alkyl of one to four carbon atoms, alkoxy of one to four carbon atoms, and halogen, and pharmaceutically acceptable salts thereof.

Suitable thiazolo- and oxazolo-quinolinamine and pyridinamine compounds include compounds of Formula IX:

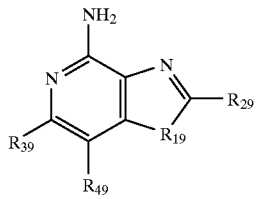

IX wherein:

$R_{19}$ is selected from the group consisting of oxygen, sulfur and selenium;

$R_{29}$ is selected from the group consisting of
—hydrogen;
—alkyl;
—alkyl—OH;
—haloalkyl;
—alkenyl;
—alkyl-X-alkyl;
—alkyl-X-alkenyl;
—alkenyl-X-alkyl;
—alkenyl-X-alkenyl;
—alkyl—$N(R_{59})_2$;
—alkyl—$N_3$;
—alkyl—O—C(O)—$N(R_{59})_2$;
—heterocyclyl;
—alkyl-X-heterocyclyl;
—alkenyl-X-heterocyclyl;
—aryl;
—alkyl-X-aryl;
—alkenyl-X-aryl;
—heteroaryl;
—alkyl-X-heteroaryl; and
—alkenyl-X-heteroaryl;

$R_{39}$ and $R_{49}$ are each independently:
—hydrogen;
—X-alkyl;
—halo;
—haloalkyl;
—$N(R_{59})_2$;
or when taken together, $R_{39}$ and $R_{49}$ form a fused aromatic, heteroaromatic, cycloalkyl or heterocyclic ring;

X is selected from the group consisting of —O—, —S—, —$NR_{59}$—, —C(O)—, —C(O)O—, —OC(O)—, and a bond; and each $R_{59}$ is independently H or $C_{1-8}$alkyl;

Suitable imidazonaphthyridine and tetrahydroimidazomaphthyridine IRM compounds are those of Formulae X and XI below:

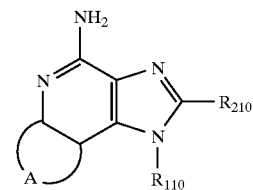

X wherein

A is =N—CR=CR—CR=; =CR—N=CR—CR=; =CR—CR=N—CR=; or =CR—CR=CR—N=;

$R_{110}$ is selected from the group consisting of:
—hydrogen;
—$C_{1-20}$ alkyl or $C_{2-20}$ alkenyl that is unsubstituted or substituted by one or more substituents selected from the group consisting of:
—aryl;
—heteroaryl;
—heterocyclyl;
—O—$C_{1-20}$ alkyl,
—O—$(C_{1-20}$alkyl$)_{0-1}$-aryl;
—O—$(C_{1-20}$alkyl$)_{0-1}$-heteroaryl;
—O—$(C_{1-20}$alkyl$)_{0-1}$-heterocyclyl;
—$C_{1-20}$ alkoxycarbonyl;
—$S(O)_{0-2}$—$C_{1-20}$ alkyl;
—$S(O)_{0-2}$—$(C_{1-20}$ alkyl$)_{0-1}$-aryl;
—$S(O)_{0-2}$—$(C_{1-20}$ alkyl$)_{0-1}$-heteroaryl;
—$S(O)_{0-2}$—$(C_{1-20}$ alkyl$)_{0-1}$-heterocyclyl;
—$N(R_{310})_2$;

—$N_3$;
oxo;
—halogen;
—$NO_2$;
—OH; and
—SH; and
—$C_{1-20}$ alkyl—$NR_{310}$—Q—X—$R_{410}$ or —$C_{2-20}$ alkenyl-$NR_{310}$—Q—X—$R_{410}$ wherein Q is —CO— or —$SO_2$—; X is a bond, —O— or —$NR_{310}$— and $R_{410}$ is aryl; heteroaryl; heterocyclyl; or —$C_{1-20}$ alkyl or $C_{2-20}$ alkenyl that is unsubstituted or substituted by one or more substituents selected from the group consisting of:
—aryl;
—heteroaryl;
—heterocyclyl;
—O—$C_{1-20}$ alkyl,
—O—$(C_{1-20}alkyl)_{0-1}$-aryl;
—O—$(C_{1-20}alkyl)_{0-1}$-heteroaryl;
—O—$(C_{1-20}alkyl)_{0-1}$-heterocyclyl;
—$C_{1-20}$ alkoxycarbonyl;
—$S(O)_{0-2}$—$C_{1-20}$ alkyl;
—$S(O)_{0-2}$—$(C_{1-20}$ alkyl$)_{0-1}$-aryl;
—$S(O)_{0-2}$—$(C_{1-20}$ alkyl$)_{0-1}$-heteroaryl;
—$S(O)_{0-2}$—$(C_{1-20}$ alkyl$)_{0-1}$-heterocyclyl;
—$N(R_{310})_2$;
—$NR_{310}$—CO—O—$C_{1-20}$alkyl;
—$N_3$;
oxo;
—halogen;
—$NO_2$;
—OH; and
—SH; or $R_{410}$ is

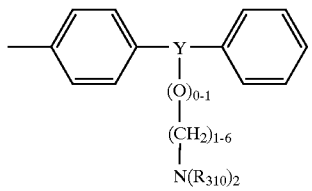

wherein Y is —N— or —CR—;
$R_{210}$ is selected from the group consisting of:
—hydrogen;
—$C_{1-10}$ alkyl;
—$C_{2-10}$ alkenyl;
—aryl;
—$C_{1-10}$ alkyl —O—$C_{1-10}$-alkyl;
—$C_{1-10}$ alkyl-O—$C_{2-10}$ alkenyl; and
—$C_{1-10}$ alkyl or $C_{2-10}$ alkenyl substituted by one or more substituents selected from the group consisting of:
—OH;
—halogen;
—$N(R_{310})_2$;
—CO—$N(R_{310})_2$;
—CO—$C_{1-10}$ alkyl;
—$N_3$;
—aryl;
—heteroaryl;
—heterocyclyl;
—CO-aryl; and
—CO-heteroaryl;
each $R_{310}$ is independently selected from the group consisting of hydrogen and $C_{1-10}$ alkyl; and each R is independently selected from the group consisting of hydrogen, $C_{1-10}$ alkyl, $C_{1-10}$ alkoxy, halogen and trifluoromethyl, or a pharmaceutically acceptable salt thereof.

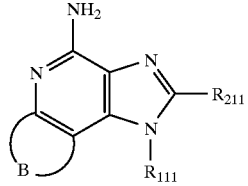

XI wherein
B is —NR—$C(R)_2$—$C(R)_2$—$C(R)_2$—; —$C(R)_2$—NR—$C(R)_2$—$C(R)_2$—; —$C(R)_2$—$C(R)_2$—NR—$C(R)_2$— or —$C(R)_2$—$C(R)_2$—$C(R)_2$—NR—;
$R_{111}$ is selected from the group consisting of:
—hydrogen;
—$C_{1-20}$ alkyl or $C_{2-20}$ alkenyl that is unsubstituted or substituted by one or more substituents selected from the group consisting of:
—aryl;
—heteroaryl;
—heterocyclyl;
—O—$C_{1-20}$ alkyl;
—O—$(C_{1-20}alkyl)_{0-1}$-aryl;
—O—$(C_{1-20}alkyl)_{0-1}$-heteroaryl;
—O—$(C_{1-20}alkyl)_{0-1}$-heterocyclyl;
—$C_{1-20}$ alkoxycarbonyl;
—$S(O)_{0-2}$—$C_{1-20}$ alkyl;
—$S(O)_{0-2}$—$(C_{1-20}$ alkyl$)_{0-1}$-aryl;
—$S(O)_{0-2}$—$(C_{1-20}$ alkyl$)_{0-1}$-heteroaryl;
—$S(O)_{0-2}$—$(C_{1-20}$ alkyl$)_{0-1}$-heterocyclyl;
—$N(R_{311})_2$;
—$N_3$;
oxo;
—halogen;
—$NO_2$;
—OH; and
—SH; and
—$C_{1-20}$ alkyl-$NR_{311}$—Q—X—$R_{411}$ or —$C_{2-20}$ alkenyl—$NR_{311}$—Q—X—$R_{411}$ wherein Q —CO— or —$SO_2$—; X is a bond, —O— or —$NR_{311}$— and $R_{411}$ is aryl; heteroaryl; heterocyclyl; or —$C_{1-20}$ alkyl or $C_{2-20}$ alkenyl that is unsubstituted or substituted by one or more substituents selected from the group consisting of:
—aryl;
—heteroaryl;
—heterocyclyl;
—O—$C_{1-20}$ alkyl,
—O—$(C_{1-20}alkyl)_{0-1}$-aryl;
—O—$(C_{1-20}alkyl)_{0-1}$-heteroaryl;
—O—$(C_{1-20}alkyl)_{0-1}$-heterocyclyl;
—$C_{1-20}$ alkoxycarbonyl;
—$S(O)_{0-2}$—$C_{1-20}$ alkyl;
—$S(O)_{0-2}$—$(C_{1-20}$ alkyl$)_{0-1}$-aryl;
—$S(O)_{0-2}$—$(C_{1-20}$ alkyl$)_{0-1}$-heteroaryl;
—$S(O)_{0-2}$—$(C_{1-20}$ alkyl$)_{0-1}$-heterocyclyl;
—$N(R_{311})_2$;
—$NR_{311}$—CO—O—$C_{1-20}$alkyl;
—$N_3$;
oxo;
—halogen;

—$NO_2$;
—OH; and
—SH; or $R_{411}$ is

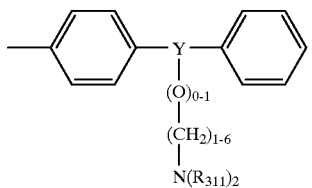

wherein Y is —N— or —CR—;
$R_{211}$ is selected from the group consisting of:
—hydrogen;
—$C_{1-10}$ alkyl;
—$C_{2-10}$ alkenyl;
—aryl
—$C_{1-10}$ alkyl-O—$C_{1-10}$-alkyl;
—$C_{1-10}$ alkyl-O—$C_{2-10}$ alkenyl; and
—$C_{1-10}$ alkyl or $C_{2-10}$ alkenyl substituted by one or more substituents selected from the group consisting of:
—OH;
—halogen;
—$N(R_{311})_2$;
—CO—$N(R_{311})_2$;
—CO—$C_{1-10}$ alkyl;
—$N_3$;
—aryl;
—heteroaryl;
—heterocyclyl;
—CO-aryl; and
—CO-heteroaryl;
each $R_{311}$ is independently selected from the group consisting of hydrogen and $C_{1-10}$ alkyl; and
each R is independently selected from the group consisting of hydrogen, $C_{1-10}$ alkyl, $C_{1-10}$ alkoxy, halogen and trifluoromethyl, and pharmaceutically acceptable salts thereof.

The compounds recited above are disclosed in the patents and applications noted above in the background, all of which are incorporated herein by reference.

The substituents $R_{11}$–$R_{111}$ above are generally designated "1-substituents" herein. The preferred 1-substituents are alkyl containing one to six carbon atoms and hydroxyalkyl containing one to six carbon atoms. More preferably the 1-substituent is 2-methylpropyl or 2-hydroxy-2-methylpropyl.

The substituents $R_{21}$–$R_{211}$ above are generally designated "2-substituents" herein. The preferred 2-substituents are hydrogen, alkyl of one to six carbon atoms, alkoxyalkyl wherein the alkoxy moiety contains one to four carbon atoms and the alkyl moiety contains one to four carbon atoms, and hydroxyalkyl of one to four carbon atoms. More preferably the 2-substituent is hydrogen, methyl, butyl, propyl hydroxymethyl, ethoxymethyl or methoxyethyl.

In instances where n can be zero, one, or two, n is preferably zero or one.

Preferred IRM Pharmaceutical Formulations

The amount of an IRM compound that will be therapeutically effective in a specific situation will depend on such things as the activity of the particular compound, the mode of administration, the particular formulation and the condition being treated. As such, it is not practical to identify specific administration amounts herein; however, those skilled in the art will be able to determine appropriate therapeutically effective amounts based on the guidance provided herein, information available in the art pertaining to these compounds, and routine testing. As used herein, the term "a therapeutically effective amount" means an amount of the compound sufficient to induce a therapeutic effect, such as cytokine induction, antiviral or antitumor activity.

The pharmaceutical formulations described below can be used for topical administration of an IRM. Many of the formulations provided are particularly advantageous for topical administration to a mucosal surface. In some embodiments, the formulations can affect the pharmacokinetics of the IRM such that reduced concentrations of the IRM provide similar pharmacodynamic affects as that of other formulations having a greater IRM concentration.

Generally, a pharmaceutical formulation of the invention includes an IRM, a fatty acid, a preservative system and a viscosity enhancing agent such as a carbomer. The IRMs can be prepared using methods previously described in the patents listed in the background section above as well as in U.S. Pat. Nos. 4,988,815; 5,367,076; 5,175,296; 5,395,937; and 5,741,908, the disclosures which are incorporated herein by reference. Unless otherwise specified, all percentages are weight percentages based on the total composition weight.

The amount of an IRM present in a pharmaceutical formulation of the invention will be an amount effective to treat a targeted condition, to prevent recurrence of the condition, or to promote immunity against the condition. The amount of IRM is preferably about 0.1% to about 9% by weight based on the total formulation weight. Preferably the IRM amount does not exceed about 5% by weight and most preferably is about 0.1 to about 3% by weight for mucosal surface applications.

Typically, a pharmaceutical formulation of the invention is an oil in water emulsion. The oil component of the formulation includes an IRM and a fatty acid. The fatty acid is present in the formulation in an amount sufficient to solubilize the IRM. This is generally about 2% to about 45%, typically about 10% to about 30%, and preferably about 15% to about 18% based on the total weight of the formulation. Fatty acids such as isostearic acid are suitable for the formulations. Alternatively, the IRM can be solubilized in linear chain carboxylic acids of six to eight carbon atoms.

A pharmaceutical formulation of the invention can also include an emulsifier such as a non-ionic surfactant. Suitable surfactants include, for example, polysorbate 60, sorbitan monostearate, polyglyceryl-4 oleate, polyoxyethylene(4) lauryl ether, etc. For some formulations, surfactants such as Poloxamers (e.g., Pluronic F68 available from BASF, Ludwigschafen, Germany) and sorbitan trioleate (e.g., Span 85 available from Sigma Chemical Co., St. Louis, Mo.), alone or in combination, are preferred. The non-ionic surfactant is typically present in an amount of about 0.5% to about 10% of total formulation weight. In preferred embodiments, the total emulsifier content does not exceed about 5% of total formulation weight, and is more preferably about 3.5% of total formulation weight.

A formulation of the invention can also include a viscosity enhancing agent such as a carbomer, preferably having mucoadhesive properties. The carbomer can be present in an amount of about 0.1% to about 8%, preferably about 0.5% to about 4%, more preferably about 0.5 to about 3%, and most preferably about 1.0% of total formulation weight. Suitable carbomers include polyacrylic acids such as Carbopol 934P, Carbopol 971P, Carbopol 940 and Carbopol 974P available from B.F. Goodrich. A preferred carbomer is Carbopol 974P.

In some embodiments, the formulation can also include a chelating agent. The chelating agent functions to chelate metal ions. If present, unchelated metal ions can suppress gel formation by suppressing ionization which facilitates gel formation in a carbomer containing formulation. A preferred chelating agent is disodium ethylenediaminetetraacetate (EDTA) in a concentration of about 0.0001 to about 0.5%, typically about 0.0005 to about 0.1% per total formulation weight.

A preservative such as methylparaben, sorbic acid, propylene glycol, etc. can also be added. In one preferred embodiment, methylparaben and sorbic acid are each provided at concentrations of about 0.05% to about 0.3%, preferably about 0.15% of total formulation weight and propylene glycol is present in amounts up to about 30%, preferably about 5%. It was discovered that this combination of preservatives advantageously meets the Preservation Effectiveness Test (PET), 1997 European Pharmacopeia, Test 5.1.3 Efficacy Antimicrobial Preservation—Topical Preparations—A Criteria. This renders the formulation suitable for use in a multi-dose dispenser without adversely affecting the stability of the formulation. The methylparaben and sorbic acid can be solubilized in propylene glycol prior to adding to the formulation.

The remainder of the pharmaceutical formulation can be comprised of water to provide a formulation that can be washed away from the mucosal surface by normal physiological clearing mechanisms.

In addition to providing mucoadhesive properties to the formulation, the carbomer also increases viscosity by forming a stabilizing gel. Many factors, such as the amount of oil phase, the drug load, and the amount of carbomer used will affect the pH at which gelation occurs. In some formulations, the presence of metal ions and surfactants increases the pH at which the carbomer will form a gel. Thus, in the absence of a chelating agent, or in the presence of increased surfactant levels, the pH at which the carbomer will gel can be increased. Thus it may be necessary to add an organic or inorganic base or other substance to facilitate gel formation. Suitable inorganic bases include, for example, KOH, NaOH, etc. The pH for a pharmaceutical formulation of the invention is typically about pH 3.0 to about pH 7.0, preferably about pH 4.0 to about pH 6.0.

Mucosal Surface Applications

According to the invention, the compositions can be applied topically, particularly to non-cornified epithelial surfaces such as mucosal surfaces. Mucosal surfaces include mucosal membranes such as buccal, gingival, nasal, tracheal, bronchial, gastrointestinal, rectal, urethral, ureteral, vaginal, cervical, uterine, etc. Depending on the IRM concentration, formulation composition, and mucosal surface, the therapeutic affect of the IRM may extend only to the superficial layers of the mucosal surface or to tissues deep to the surface.

In one embodiment, the disclosed IRMs can be topically applied to the vaginal or supravaginal region of the cervix for treatment of dysplastic conditions such as cervical intraepithelial neoplasia. In some embodiments, the above described formulations are particularly advantageous for cervical application of an IRM for a period of time sufficient to obtain a desired therapeutic effect without undesired systemic absorption of the IRM.

Cervical Intraepithelial Neoplasia (CIN)

Approximately 16,000 new cases of invasive cancer of the cervix are diagnosed each year in the U.S. despite extensive screening of women to detect predictive cellular changes. There are also about 3,000 deaths due to cervical cancer in the U.S. alone and this is usually secondary to not detecting the primary cancerous lesion in a timely manner.

The Papanicoulaou Test (Pap smear) is the screening test which has been accepted since the 1950s as the method to detect abnormal cells of the cervix, including inflammation and dysplasia, which includes cervical cancer. This screening test has been widely adopted in industrialized countries and has had a profound impact on mortality associated with cervical cancers. An abnormal Pap smear prompts close observation for disease progression with the potential for the therapeutic interventions of destruction or excision of cancerous or pre-cancerous tissues. These excisional treatments are expensive, uncomfortable and associated with failure rates which range from 2 to 23% and with higher failure rates reported for the more advanced lesions. Failure rates have recently been documented to approximate 10% following laser treatment.

The etiologic agent for cervical cancer was originally thought to be the herpes virus. However, there was a gradual shift from this focus on herpes virus to the human papillomavirus (HPV) when it was shown that the cytopathic effects of HPV in experimental systems very closely mimicked what was seen in human disease. Improved experimental methods over the recent past have allowed the characterization of a full spectrum of HPV subtypes, which has resulted in the conclusion that the high risk HPV types (e.g., HPV 16, 18, and less frequently 31, 33, 35, 45) are very likely the exclusive initiating factor (i.e., oncogenic agent) for cervical dysplasia and subsequent cancers. The mechanism of HPV transformation of the normal cell to a dysplastic cell is associated with the HPV encoded oncoproteins (E6 and E7) from the high risk genotypes binding the cell's tumor suppressor gene products p53 and Rb resulting in disruption of the cell cycle control mechanism in which p53 and Rb play an important role. In addition, the application of these molecular methods has resulted in the epidemilogic observation that HPV is isolated from approximately 93% of cervical tumors, which has further strengthened the generally accepted conclusion that HPV infection is the most important initiating agent for cervical cancer.

Exposure to HPV is common in sexually active women, but it does not invariably lead to dysplasia or cancer in most of the exposed women. Infected women who harbor persistent viral DNA have about five times the chance of persistent dysplasia compared to women who are able to eradicate the virus. The importance of cell-mediated immune (CMI) response to HPV infection is illustrated by the observation that the antibody mediated immune response is not effective in eliminating established infections as is demonstrated by the fact that patients with invasive cervical dancer often exhibit high antibody levels against the viral E6 and E7 proteins. This particular antibody response probably reflects extensive antigen exposure in the face of increasing tumor burden. In contrast to the apparently inconsequential effect of the humoral immune response, the cell-mediated immune response (Th-1-Type Response) appears to be effective in controlling tumor progression. Regression of intraepithelial lesions is accompanied by a cellular infiltrate consisting of $CD4^+$ T-CELLS, $CD8^+$ T-CELLS, natural killer cells (NK) and macrophages. This inflammatory infiltrate was usually associated with tumor regression which is in contrast to women who lack the ability to mount this inflammatory response and who experience disease progression. In addition, patients with a defect in cell-mediated immunity have increased cervical cancer rates, whereas those with defects in the production of antibody do not exhibit the same susceptibility.

In one preferred embodiment, the inventors foresee the topical application of IRMs for the non-invasive treatment of cervical conditions including cervical intraepithelial neoplasia (CIN).

Intravaginal Applicators for an IRM

To obtain a beneficial therapeutic or prophylactic effect for a cervical condition, intravaginal application of a herein disclosed IRM is preferred. The IRM can be applied via a dosing formulation or dispenser which ensures contact of the IRM with the mucosal surface of the cervix for a period of time sufficient to provide the desired therapeutic effect.

In one embodiment, an IRM can be formulated as a suppository and administered intravaginally using a suppository applicator. A suitable suppository applicator includes known cardboard tube applicators for dispensing medications to the vaginal cavity.

Formulations according to the invention can also be administered using a barrel type applicator. An example of a suitable barrel type applicator can be found in U.S. Pat. No. 5,282,789, the disclosure of which is incorporated herein by reference.

In another embodiment, an IRM can be administered directly to the cervical mucosa. In one such embodiment, the IRM can be topically applied to the cervical mucosa by using a direct cervical applicator, such as a cervical cap. One example of a suitable cervical cap is found in U.S. Pat. No. 4,858,624, the disclosure of which is incorporated herein by reference. Suitable IRM formulations for direct cervical applications are disclosed above and in the Examples below. In general, an IRM formulated pursuant to any of formulations A–J in the Examples below can be placed into the concave region of the cervical cap which is then applied directly over the cervix. Preferably, the IRM is formulated to include a viscosity agent, such as a carbomer, to enhance the residence time of the IRM on the cervix.

The following Examples are provided to further describe IRM formulations and methods according to the invention. The examples, however, are not intended to limit the formulations and methods within the spirit and scope of the invention.

EXAMPLES

Example 1

Evaluation of the Safety, Pharmacokinetics (PK) and Pharmacodynamics (PD) of 1-(2-methylpropyl)-1H-Imadazo[4,5-c]quinolin-4-amine (imiquimod) Applied to the Cervix.

Methods

This was a single dose, randomized, double-blind, placebo controlled dose escalation study which evaluated five doses of imiquimod. 50, 100, 150, 200 and 250 mg of imiquimod in a cream formulation were applied to the cervix for eight hours. The ingredients of the formulation of the imiquimod cream used for this study (Formulation A) is presented in Table I below. Each dose group was composed of 8 subjects (6 active and 2 placebo), with two subjects treated as dose leaders, and the remaining six subjects were treated after an acceptable response by the dose leaders. Safety was assessed by adverse events (AE's), laboratory tests, and colposcopy with photodocumentation of the cervix at pre-dose and 24 hours post-dose, and 48 hours post-dose if required. Systemic exposure (PK) was determined by measuring imiquimod and metabolites through 48 hours post-dose and the PD response was determined by serum analysis for the cytokines: tumor necrosis factor-α(TNF-α), interferon-α(IFN-α), interleukin-1 receptor agonist (IL-1RA), interleukin-6 (IL-6), neopterin (NPT) and 2'5' oligoadenlyate synthetase (2'5' AS) during dosing and selected times during the 48 hours post-dose. Statistical tests to evaluate AE's and demographics, laboratory tests, vital signs and ECG's were Fisher's Exact, Wilcoxon Rank-Sum and Kruskall Wallis Tests respectively. Cytokine changes between dose groups were compared using Wilcoxon Rank-Sum and changes from baseline were evaluated using Spearman Rank Correlation.

Results

Thirty-nine generally healthy, surgically sterilized, 18–50 year-old females within 25% of ideal body weight were included in the study. All women had normal baseline colposcopy results with normal and borderline dyskariosis on cervical histology. AE's were reported in each of the 39 subjects with mild temperature elevation the most common event (92%). There were no differences among groups with respect to subjects who experienced one or more events, or in AE's attributed as possibly or probably related to drug. (Two serious AE's occurred which were intercurrent events associated with a fractured ankle and its surgical repair.) There were statistically significant changes in some laboratory parameters and pulse rates that were not considered clinically significant. There were no differences in ECG's or physical exams. Pelvic and colposcopic examinations revealed few reactions with 2 of 6 receiving 250 mg experiencing cervical changes of minor small vesicles or smaller ulcer. These reactions resolved within 48 hours. No quantifiable (>5 ng/ml) serum levels of imiquimod were detected. Significant changes from baseline were seen in IFN and IL-6 in the 250 mg group and in NPT. 2'5' AS and IL-1RA in the 150 mg, 200 mg, and 250 mg groups.

The study showed that single doses of imiquimod up to 250 mg applied to the cervix for 8 hours in healthy volunteers is safe with minimal systemic exposure. Cervical application of a dose ≧150 mg increases the systemic concentration of certain cytokines.

TABLE 1

| Components | Formulation A (% w/w) |
| --- | --- |
| Imiquimod | 5.0 |
| Isostearic Acid | 25.0 |
| Benzyl Alcohol | 2.0 |
| Cetyl Alcohol | 2.2 |
| Stearyl Alcohol | 3.1 |
| White Petrolatum | 3.0 |
| Polysorbate 60 | 3.4 |
| Sorbitan Monostearate | 0.6 |
| Glycerin | 2.0 |
| Methyl Paraben | 0.2 |
| Propyl Paraben | 0.02 |
| Water | 52.98 |
| Xanthan Gum | 0.5 |
| PH | 5.1 |
| Viscosity (cps) | $0.33 \times 10^5$ |

Example 2

Preparation of Pharmaceutical Formulation B

This example describes a novel formulation for a vaginal application, that is a stable formulation, with a high viscosity, and well preserved to pass the EP preservative effectiveness test (PET) criteria. The w/w % of ingredients of this formulation (Formulation B) are shown in Table 2 below.

Imiquimod was dissolved in isostearic acid with Span 85. Pluronic F68, EDTA, Carbopol 974P, propylene glycol, sorbic acid, and methylparaben were dissolved in water. After emulsification to form an oil-in-water emulsion, sodium hydroxide was added to achieve a pH of about 5.2. The pH range for this formulation can be about 4.8 to 6.0.

TABLE 2

| Compounds | Formulation B (% w/w) |
| --- | --- |
| Imiquimod | 5 |
| Isostearic acid | 28 |
| Pluronic F68 | 2.98 |
| Purified water | 43.78 |
| Carbopol 974P | 1.7 |
| Disodium EDTA | 0.05 |
| Propylene glycol | 15 |
| Sorbic acid | 0.15 |
| Methylparaben | 0.15 |
| Span 85 | 2.02 |
| 5N NaOH | 1.17 |
| PH | 5.1 |
| Viscosity (cps) | $6.4 \times 10^5$ |

Example 3
Preparation of Pharmaceutical Formulations C–F

Pharmaceutical Formulations C–F were prepared with the components recited below in Table 3. The method for preparing Formulations C–F was the same as that disclosed for preparing Formulation B in Example 2.

TABLE 3

| Composition | Formulation C (% w/w) | Formulation D (% w/w) | Formulation E (% w/w) | Formulation F (% w/w) |
| --- | --- | --- | --- | --- |
| Imiquimod | 1.0 | 1.0 | 3.0 | 3.0 |
| Isostearic acid | 5.6 | 28.0 | 16.8 | 28.0 |
| Pluronic F68 | 1.79 | 1.79 | 1.79 | 1.79 |
| Purified water | 69.05 | 48.30 | 56.25 | 46.75 |
| Carbopol 974P | 2.8 | 2.10 | 2.5 | 1.80 |
| Disodium EDTA | 0.05 | 0.05 | 0.05 | 0.05 |
| PG* | 15.0 | 15.0 | 15.0 | 15.0 |
| Sorbic acid | 0.15 | 0.15 | 0.15 | 0.15 |
| Methylparaben | 0.15 | 0.15 | 0.15 | 0.15 |
| Span 85 | 1.21 | 1.21 | 1.21 | 1.21 |
| 5N NaOH | 3.2 | 2.26 | 3.1 | 2.1 |
| pH | 5.1 | 5.2 | 5.2 | 5.3 |
| Viscosity (cps) | $5.8 \times 10^5$ | $8.8 \times 10^5$ | $11.0 \times 10^5$ | $10.0 \times 10^5$ |

*PG is Propylene glycol

Example 4
Imiquimod Transport Across Hairless Mouse Skin from Two Formulations A and B, both at 5% w/w Imiquimod.

FIG. 1 is a graph of the results of imiquimod penetration studies of Formulations A and B, of Examples 1 and 2, using hairless mouse skin according to the procedure described in U.S. Pat. No. 5,238,944, the entire disclosure of which is incorporated herein by reference.

In brief, hairless mouse skin was removed from female hairless mice that were 5 to 7 weeks old (available from Charles River). The skin was maintained on ice until used. The mouse skin was mounted on a diffusion cell of the type shown in U.S. Pat. No. 5,238,944. The mouse skin was mounted with the epidermal side up between upper and lower portions of the cell which are held together by means of ball joint clamp.

The portion of the cell below the mounted skin was completely filled with 0.1 N HCl receptor fluid such that the receptor fluid contacted the skin. The receptor fluid was stirred using a magnetic stir bar and a magnetic stirrer.

Approximately 100±5 mg formulation to be tested was applied to the epidermal (upper) side of the skin to cover in an even layer only the area of skin that would be in contact with the receptor fluid when the skin was mounted in the diffusion cell. The formulations were applied to the skin prior to the time the receptor fluid was added to the cell below the skin.

The cell was then placed in a constant temperature (31° C.) chamber. To maintain constant temperature, the chamber utilized a heat exchanger coupled to a constant temperature bath, with a fan to circulate air. The receptor fluid was stirred by means of a magnetic stirring bar throughout the experiment to ensure a uniform sample and a reduced diffusion barrier layer on the dermal side of the skin. At specified time intervals (1, 2, 4, 6, 8, 12 and 24 hours), the entire volume of receptor fluid was removed and immediately replaced with fresh receptor fluid. The withdrawn receptor fluid was analyzed for imiquimod content by conventional high pressure chromatography as follows:

Detector: UV at 258 nm; Mobile Phase: 25/75 acetonitrile/water containing 1% triethylamine, 0.2% 1-octane sulfonate with the pH adjusted to 2.0 with $H_3PO_4$; Stationary Phase: C8 Zorbax RX-C8 5 $\mu$; Flow Rate: 2 ml/min; Run Time: approximately 10 minutes.

Cumulative amount of penetration was plotted versus time to obtain the steady state rate.

Example 5
Imiquimod Transport Across Nude Mouse skin from Formulations C–F at 1% w/w and 3% w/w Imiquimod with Varied Concentrations of Isostearic Acid (ISA).

Figure 2:
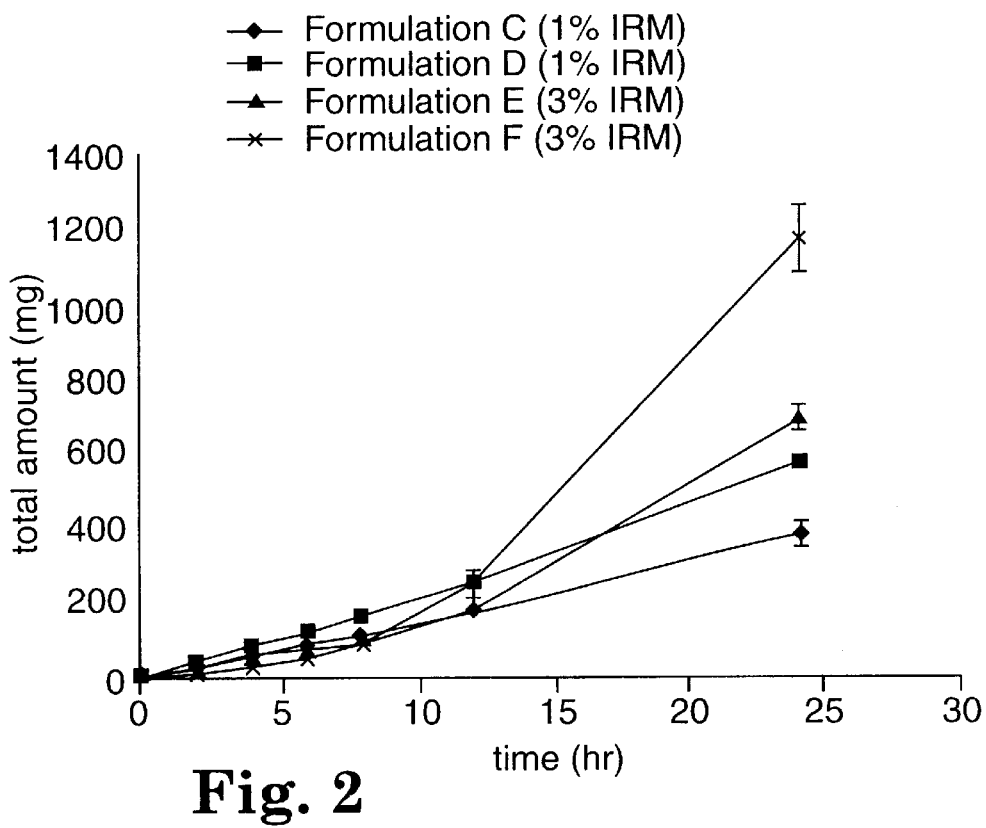
FIG. 2 is a graph comparing imiquimod transport across hairless mouse skin from four pharmaceutical formulations containing varied concentrations of imiquimod and isostearic acid.

Table 4 below provides the imiquimod concentration, isostearic acid concentration, viscosity, pH and steady state rate ($\mu$g/hour) of Formulations C–F across nude mouse skin. The results are graphed in FIG. 2. The procedure used to study skin penetration was the same as that disclosed in Example 4.

TABLE 4

| Formulation | IRM Concentration (% w/w) | ISA Concentration (% w/w) | Viscosity ($\times 10^{-5}$ cps) | Steady State Rate ($\mu$g/hr) |
| --- | --- | --- | --- | --- |
| C | 1% | 5.6% | 5.8 | 18.1 |
| D | 1% | 28% | 8.8 | 26.1 |
| E | 3% | 16.8% | 11 | 39.9 |
| F | 3% | 28% | 10 | 71.5 |

Example 6
Pharmacokinetics Comparison of Imiquimod in Rats after Single Dose Vaginal Application of Formulation A and Formulation B Serum imiquimod concentration versus time profiles were compared in ovariectomized rats after single intravaginal doses of Formulation A or Formulation B. The two 5% w/w formulations were dosed to provide a dose level of 35 mg/kg. After dosing, each rat was collared to prevent removal of the formulation by licking. After about six hours, the vagina was lavaged and the collars removed. Blood samples were collected at pre-dose and at 0.5, 1, 2, 3, 4 and 24 hours post-dose. Due to the higher viscosity of Formulation B, intravaginal administration to the rats was considerably easier and retention of Formulation B was superior to Formulation A.

Figure 3:
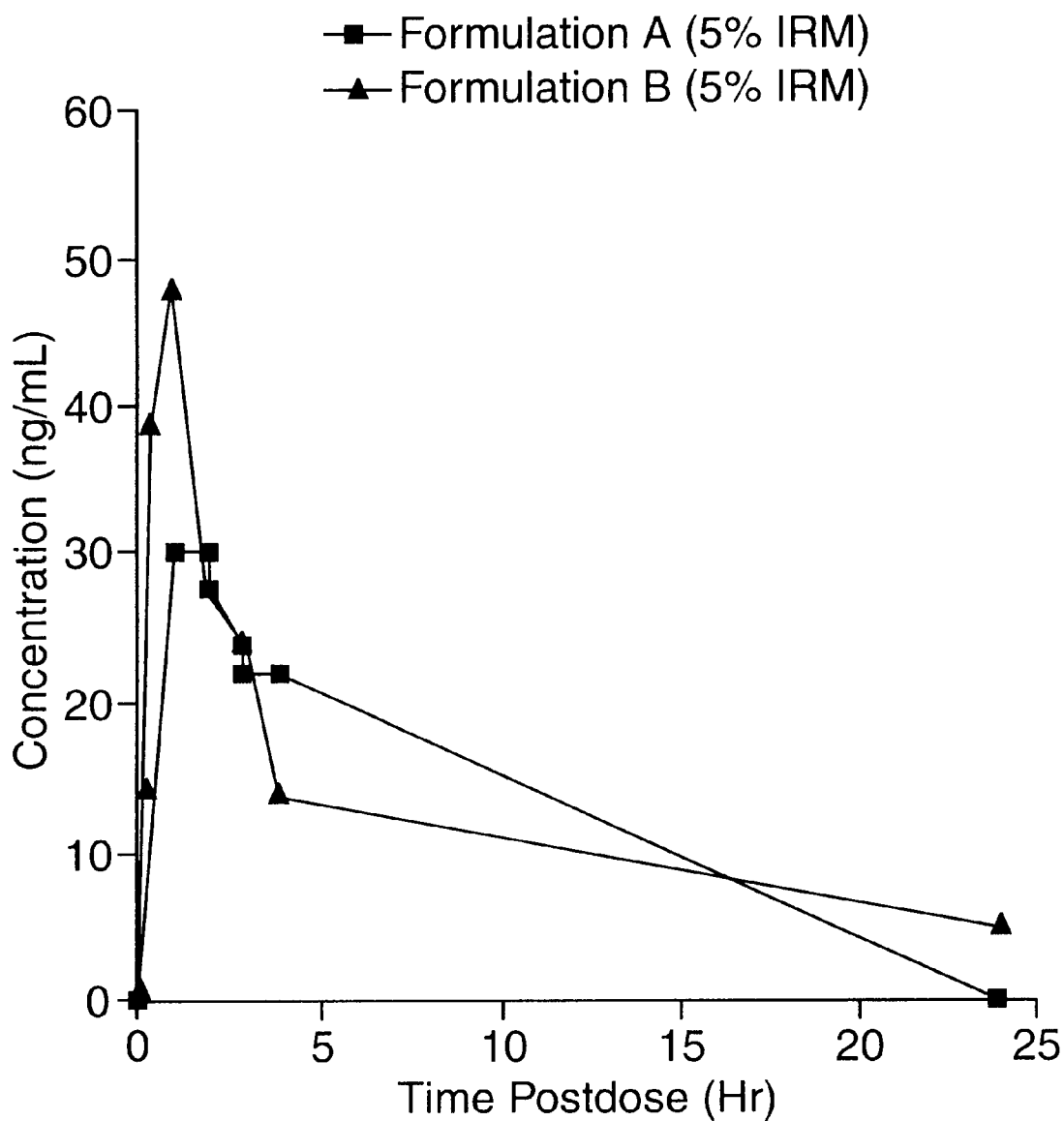
FIG. 3 is a graph comparing mean serum imiquimod concentration in rats after a single intravaginal dose of Formulation A or Formulation B.
Figure 4A:
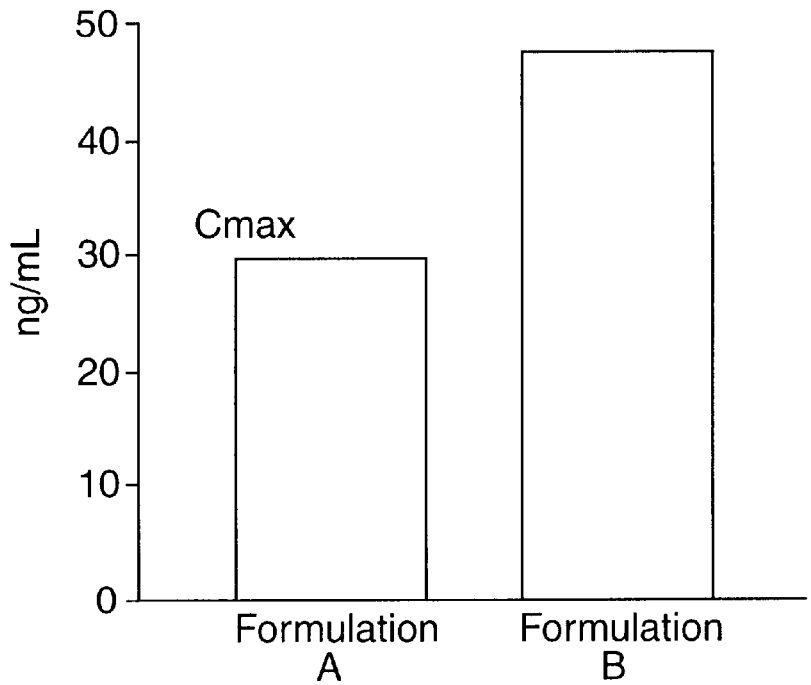
FIG. 4 provides bar graphs of the pharmacokinetic comparison of imiquimod in rats after vaginal dosing of Formulation A or Formulation B.
Figure 4B:
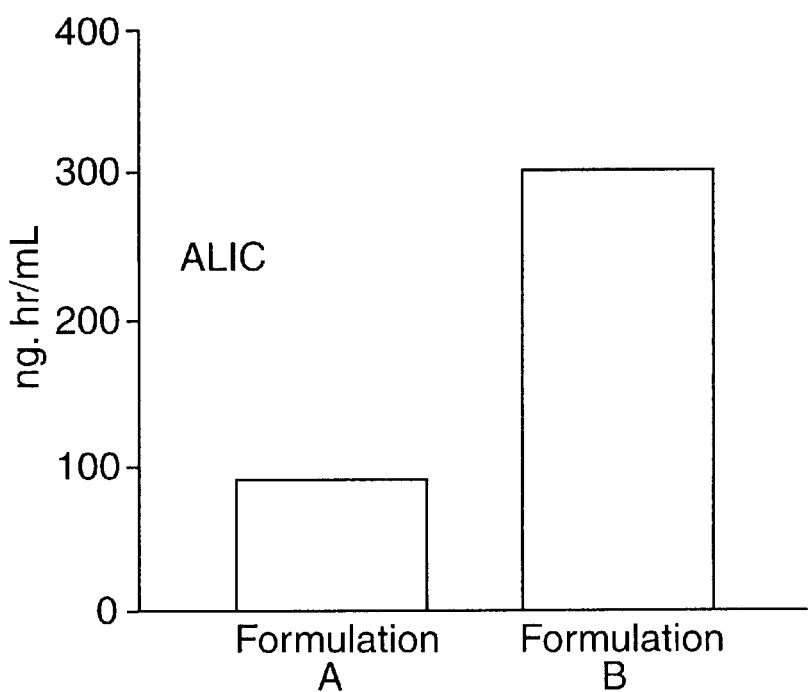

Serum was analyzed by HPLC for imiquimod. Mean serum imiquimod concentrations versus time are depicted in FIG. 3. The time to achieve maximum serum concentrations of imiquimod ($T_{max}$) was similar (1 hr) for both formulations. However, the maximum imiquimod concentration ($C_{max}$) for Formulation B was approximately 1.6 times greater than for Formulation A and the respective area under the curve versus time (AUC) was 3.3 times greater (FIG. 4).

Based upon these data, the rate and extent of absorption of imiquimod was greater from Formulation B than from Formulation A.

Example 7
Preparation of Pharmaceutical Formulation G

The w/w % of the ingredients for Formulation G are shown in Table 5.

An oil phase was prepared as follows. Imiquimod (20.0 g) was slowly added with stirring to isostearic acid (3000 g). The mixture was stirred and heated, as necessary, up to 55° C. to facilitate dissolution of the imiquimod. After dissolution was complete the heat was turned off. Sorbitan trioleate (200 g) was added and thoroughly mixed. Carbomer 974 was slowly added with mixing. The mixing was continued until the carbomer was uniformly dispersed in the oil phase. The oil phase was then allowed to cool to a temperature of less than 30° C.

An aqueous phase was prepared as follows. Sorbic acid (30.0 g) and methylparaben (40.0g) were added with stirring to propylene glycol (1000 g). The resulting mixture was stirred and heated gently (<45° C.) until a solution was obtained. The heat source was removed. Polaxamer 188 (500 g) was added to the solution. The resulting mixture was stirred until the polaxamer was thoroughly wet. The resulting slurry was then added to a solution of edetate disodium (10.0 g) in purified water (13950 g). The resulting mixture was stirred until a clear solution was obtained.

A sodium hydroxide solution was prepared by dissolving sodium hydroxide pellets (50 g) in purified water (1000 g).

The oil phase was added to the aqueous phase and then the sodium hydroxide solution was added. The resulting mixture was mixed for a minimum of 30 minutes until a smooth and shiny cream was obtained. The pH was determined and adjusted, if necessary, to 5.6–5.8 with sodium hydroxide solution.

Example 8
Preparation of Pharmaceutical Formulations H–J Pharmaceutical formulations H–J were prepared using the method of Example 7. The w/w % of the ingredients in the formulations is shown in Table 5 below.

TABLE 5

| Formulation Component | G % w/w | H % w/w | I % w/w | J % w/w |
|---|---|---|---|---|
| Isostearic Acid (874) | 15.00 | 15.00 | 15.00 | 18.00 |
| Imiquimod | 0.10 | 0.50 | 1.50 | 3.00 |
| Sorbitan Trioleate | 1.00 | 1.00 | 1.00 | 1.00 |
| Propylene Glycol | 5.00 | 5.00 | 5.00 | 5.00 |
| Sorbic Acid | 0.15 | 0.15 | 0.15 | 0.15 |
| Methylparaben | 0.20 | 0.20 | 0.20 | 0.20 |
| Purified Water | 75.00 | 74.60 | 73.60 | 69.10 |
| Edetate Disodium | 0.05 | 0.05 | 0.05 | 0.05 |
| Polaxamer 188 | 2.50 | 2.50 | 2.50 | 2.50 |
| Carbomer 974 | 1.00 | 1.00 | 1.00 | 1.00 |
| Sodium Hydroxide | qs | qs | qs | Qs |
| Total % w/w | 100 | 100 | 100 | 100 |

Accordingly, from the foregoing discussion, it will appreciated that the imidazoquinoline amines, imidazopyridine amines, 6,7-fused cycloalkylimidazopyridine amines, and 1,2-bridged imidazoquinoline amines of the present invention can be beneficial for treating mucosal associated conditions including cervical dysplasias. In addition, the disclosed pharmaceutical formulations can be particularly advantageous for topical application of an IRM to a mucosal surface.

From the foregoing detailed description and examples, it will be evident that modifications and variations can be made in the formulations and methods of the invention without departing from the spirit or scope of the invention. Therefore, it is intended that all modifications and verifications not departing from the spirit of the invention come within the scope of the claims and their equivalents.

We claim:

1. A pharmaceutical formulation comprising:
   an immune response modifier (IRM) compound selected from the group consisting of imidazoquinoline amines, imidazopyridine amines, 6,7-fused cycloalkylimidazopyridine amines, 1,2-bridged imidazoquinoline amines, thiazolo- and oxazolo-quinolinamines and pyridinamines, imidazonaphthyridine and tetrahydroimidazonaphthyridine amines;
   a fatty acid;
   a preservative system; and
   a carbomer.

2. The formulation according to claim 1 wherein the formulation further comprises a surfactant.

3. The formulation according to claim 1 wherein the preservative system comprises methylparaben at about 0.1 to about 0.25% w/w of the formulation and sorbic acid at about 0.1 to about 0.2% w/w of the formulation.

4. The formulation according to claim 3 wherein the preservative system comprises methylparaben at about 0.2% w/w of the formulation and sorbic acid at about 0.15% w/w of the formulation.

5. The formulation of claim 1 comprising:
   (a) about 0.1 to about 9% w/w 1-(2-methylpropyl)-1H-imidazo [4,5-c]-quinoline-4-amine;
   (b) about 2 to about 30% w/w isostearic acid;
   (c) about 0.5 to about 5% w/w surfactant;
   (d) about 0.05 to about 20% w/w preservative; and
   (e) about 0.1 to about 8% carbomer.

6. The formulation of claim 1 comprising:
   (a) about 0.1 to about 3% w/w 1-(2-methylpropyl)-1H-imidazo[4,5-c]-quinolin-4-amine;
   (b) about 15 to about 18% w/w isostearic acid;
   (c) about 0.5 to about 3.5% w/w surfactant;
   (d) about 0.05 to about 5.5% w/w preservative; and
   (e) about 0.5 to about 1.5% w/w carbomer.

7. A method of treating a condition associated with a mucosal surface, the method comprising a step of:
   applying to the mucosal surface a therapeutically effective amount of an immune response modifier (IRM) compound selected from the group consisting of imidazoquinoline amines, imidazopyridine amines, 6,7-fused cycloalkylimidazopyridine amines, and 1,2-bridged imidazoquinoline amines.

8. The method according to claim 7 wherein the IRM is 1-(2-methylpropyl)-1H-imidazo[4,5-c]-quinolin-4-amine.

9. The method according to claim 7 wherein the mucosal surface is on a cervix.

10. The method according to claim 9 wherein the mucosal surface is on the vaginal part of the cervix.

11. The method according to claim 10 wherein the condition associated with the mucosal surface is cervical intraepithelial neoplasia.

12. A method of treating a cervical dysplasia, the method comprising a step of:
   applying to a cervix a therapeutically effective amount of an immune response modifier (IRM) compound selected from the group consisting of imidazoquinoline amines, imidazopyridine amines, 6,7-fused cycloalkylimidazopyridine amines, and 1,2-bridged imidazoquinoline amines.

13. The method according to claim 12 wherein the IRM is 1-(2-methylpropyl)-1H-imidazo[4,5-c]-quinolin-4-amine.

14. The method according to claim 12 wherein the immune response modifier is 4-amino-2-ethoxymethyl-α,α-dimethyl-1H-imidazo[4,5-c]quinoline-1-ethanol.

15. The method according to claim 12 wherein the IRM is applied as a pharmaceutical formulation comprising:

the IRM;

a fatty acid;

a preservative system; and a carbomer.

16. The method according to claim 9 wherein the formulation further comprises a surfactant.

17. The method according to claim 15 wherein the preservative system comprises methylparaben at about 0.1 to about 0.25% w/w of the formulation and sorbic acid at about 0.1 to about 0.2% w/w of the formulation.

18. The method according to claim 17 wherein the preservative system comprises methylparaben at about 0.2% w/w of the formulation and sorbic acid at about 0.15% w/w of the formulation.

19. The method according to claim 15 wherein the formulation is contained in a multi-use dispenser.

20. A method of treating cervical intraepithelial neoplasia, the method comprising a step of:

applying to a cervix a therapeutically effective amount of an immune response modifier compound selected from the group consisting of imidazoquinoline amines, imidazopyridine amines, 6,7-fused cycloalkylimidazopyridine amines, and 1,2-bridged imidazoquinoline amines.

21. A method for delivering an immune response modifier (IRM) to a mucosal surface, the method comprising the steps of:

selecting a pharmaceutical formulation comprising:
(a) an immune response modifier selected from the group consisting of imidazoquinoline amines, imidazopyridine amines, 6,7-fused cycloalkylimidazopyridine amines, 1,2-bridged imidazoquinoline amines, thiazolo- and oxazolo-quinolinamines and pyridinamines, imidazonaphthyridine and tetrahydroimidazonaphthyridine amines;
(b) a fatty acid;
(c) a preservative system; and
(d) a carbomer; and applying the selected pharmaceutical formulation to the mucosal surface.

22. The method of claim 21 wherein the formulation is applied using a barrel type applicator.

* * * * *

UNITED STATES PATENT AND TRADEMARK OFFICE
CERTIFICATE OF CORRECTION

PATENT NO. : 6,245,776 B1
DATED : June 12, 2001
INVENTOR(S) : Raymond Skwierczynski, Kenneth R. Phares, Richard L. Miller, Zheng Jane Li, Michael J. Jozwiakowski, Terri F. Busch It is certified that error appears in the above-identified patent and that said Letters Patent is hereby corrected as shown below:

Column 1,
Line 7, "60/115,256" should read -- "60/115,253"

Signed and Sealed this

Eleventh Day of December, 2001

Attest:

NICHOLAS P. GODICI
Attesting Officer
Acting Director of the United States Patent and Trademark Office